(12) United States Patent
Greisiger et al.

(10) Patent No.: US 8,697,785 B2
(45) Date of Patent: Apr. 15, 2014

(54) N-ALLYL CARBAMATE COMPOUNDS AND USE THEREOF, IN PARTICULAR IN RADIATION-CURING COATINGS

(75) Inventors: Heinz Greisiger, Reutlingen (DE); Marc Entenmann, Fellbach (DE); Thadeus Schauer, Neuhengstett (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 13/483,918

(22) Filed: May 30, 2012

(65) Prior Publication Data

US 2012/0296021 A1    Nov. 22, 2012

Related U.S. Application Data

(63) Continuation of application No. PCT/EP2010/068342, filed on Nov. 26, 2010.

(30) Foreign Application Priority Data

Dec. 1, 2009    (DE) .......................... 10 2009 058 297

(51) Int. Cl.
C08K 5/34    (2006.01)
D21H 21/16    (2006.01)

(52) U.S. Cl.
USPC ........................................ 524/100; 106/287.2

(58) Field of Classification Search
USPC ................................ 524/198, 100; 106/287.2
See application file for complete search history.

(56) References Cited

U.S. PATENT DOCUMENTS

| | | | |
|---|---|---|---|
| 3,697,582 A | 10/1972 | Fancher | |
| 3,855,093 A | 12/1974 | Guthrie et al. | |
| 3,877,971 A * | 4/1975 | Guthrie et al. | 427/517 |
| 5,210,273 A | 5/1993 | Reiff et al. | |
| 6,686,046 B2 | 2/2004 | Schauer et al. | |
| 6,777,494 B1 * | 8/2004 | Yang et al. | 525/123 |
| 2004/0161537 A1 | 8/2004 | Schauer et al. | |
| 2004/0253444 A1 | 12/2004 | Schauer et al. | |
| 2006/0046057 A1 | 3/2006 | Huber et al. | |
| 2006/0094819 A1 | 5/2006 | Muller et al. | |
| 2007/0078213 A1 | 4/2007 | Mueller et al. | |
| 2007/0166534 A1 | 7/2007 | Entenmann et al. | |
| 2007/0166544 A1 | 7/2007 | Hennemann et al. | |
| 2008/0139691 A1 | 6/2008 | Blum et al. | |
| 2008/0168924 A1 | 7/2008 | Melson et al. | |
| 2008/0275153 A1 | 11/2008 | Hwang et al. | |
| 2009/0253805 A1 * | 10/2009 | Hoyle et al. | 514/772.3 |
| 2009/0288581 A1 | 11/2009 | Huber et al. | |
| 2009/0324945 A1 | 12/2009 | Licht et al. | |
| 2010/0197866 A1 | 8/2010 | Entemann et al. | |

FOREIGN PATENT DOCUMENTS

| | | |
|---|---|---|
| DE | 1 916 971 | 11/1969 |
| DE | 24 41 600 A1 | 3/1975 |
| DE | 24 02 390 A1 | 8/1975 |
| DE | 10 2004 042 012 A1 | 3/2006 |
| DE | 10 2004 053 186 A1 | 5/2006 |
| DE | 10 2006 049 764 A1 | 4/2008 |
| DE | 10 2008 005 826 A1 | 8/2008 |
| DE | 10 2009 055 828 A1 | 7/2010 |
| EP | 0 408 034 A1 | 1/1991 |
| EP | 0 410 214 A1 | 1/1991 |
| EP | 0 477 159 A1 | 3/1992 |
| EP | 1 111 008 A1 | 6/2001 |
| EP | 1 333 047 A1 | 8/2003 |
| EP | 1 338 623 A1 | 8/2003 |
| EP | 1 674 513 A1 | 6/2006 |
| FR | 2 258 436 | 8/1975 |
| GB | 1 485 052 | 9/1977 |
| JP | 57-133108 A | 8/1982 |
| JP | 57-158230 A | 9/1982 |
| JP | 58-213022 A | 12/1983 |
| JP | 7-69686 A | 3/1995 |
| JP | 2008-274209 A | 11/2008 |
| WO | WO 93/09084 A1 | 5/1993 |
| WO | WO 0160926 A1 | 8/2001 |
| WO | WO 03014229 A1 | 2/2003 |
| WO | WO 03014230 A1 | 2/2003 |
| WO | WO 2004/000794 A1 | 12/2003 |
| WO | WO 2004/029160 A1 | 4/2004 |

(Continued)

OTHER PUBLICATIONS

Manfredini, S. et al., *J. Med. Chem.*, 37, XP55002455, 2401-2405 (1994).

(Continued)

*Primary Examiner* — John Uselding
(74) *Attorney, Agent, or Firm* — Leydig, Voit & Mayer, Ltd.

(57) ABSTRACT

An N-allyl carbamate compound which is suitable as an additive is proposed, the chemical main body thereof allowing modifications of the overall structure of the compound in order to ensure sufficiently high compatibility with as many binder systems as possible, wherein the UV-crosslinkable double bond is designed to be as sterically undemanding as possible, linked via flexible bonds, and highly reactive. In the N-allyl carbamate compound of general formula (A) according to the invention, the radical R1 is selected from straight-chain, branched, or cyclic substituted aliphatic hydrocarbon radicals and heterocyclic radicals, wherein the radical R1 includes at least one ethylenically unsaturated bond, wherein R2, R3, and R4 are selected from hydrogen and hydrocarbon radicals, wherein R5 represents hydrogen or an allyl group, and wherein c is an integer of 1 or greater.

23 Claims, No Drawings

(56) References Cited

FOREIGN PATENT DOCUMENTS

| WO | WO 2005/047369 A2 | 5/2005 |
|----|-------------------|--------|
| WO | WO 2005/056696 A2 | 6/2005 |
| WO | WO 2005/075578 A2 | 8/2005 |
| WO | WO 2006/018169 A1 | 2/2006 |
| WO | WO 2006/018196 A1 | 2/2006 |
| WO | WO 2007/017285 A1 | 2/2007 |
| WO | WO 2008/049932 A1 | 5/2008 |
| WO | WO 2010/063430 A1 | 6/2010 |
| WO | WO 2010/136122 A1 | 12/2010 |
| WO | WO 2010/136123 A1 | 12/2010 |
| WO | WO 2010/136124 A1 | 12/2010 |

OTHER PUBLICATIONS

Martin R., et al., *The Journal of Organic Chemistry*, 70, (6), XP55002515, 2325-2328 (2005).

Simoni, D. et al., *J. Med. Chem.*, 34, XP002311503, 3172-3176 (1991).

International Search Report, Application No. PCT/EP2010/068342, dated Jul. 26, 2011.

International Preliminary Report on Patentability, Application No. PCT/EP2010/068342, mailed Jun. 14, 2012.

Wright, "European Coatings Show 2011," *Coatings World*, 50-53, May 2011.

Entenmann et al. "A Finer Level of Defence," *Corrosion Management*, 104: 10-13 (2011).

Entenmann et al. "Novel UV-curable clearcoats it improved chemical, mechanical, and adhesive properties," presented at European Coating Show (ECS 2013).

Entenmann et al. "Novel crosslinking additive for chemical resistant UV-curable clearcoats," *RadTech Europe 2013*; Basel.

European Coatings, "Automotive industry sees a very clear light in the development tunnel," www.european-coatings.com, Aug. 28, 2013.

* cited by examiner

N-ALLYL CARBAMATE COMPOUNDS AND USE THEREOF, IN PARTICULAR IN RADIATION-CURING COATINGS

The invention relates to novel N-allyl carbamate compounds and use thereof as a component in compositions, in particular in radiation-curing coatings, preferably UV radical-curable coating compositions.

Crosslinked polymers are used in a variety of ways. They represent important basic components of many materials, for example duroplastic molded parts, adhesive compounds, and inks, in addition to all types of coatings; ultimately, the type of crosslinking and its density are critical for mechanical and chemical properties as well as stability.

Radiation-curing coatings are often used to improve the chemical and mechanical resistance of the coated substrates, in particular resistance to reagents having an alkaline or acidic effect. In this regard, UV-curing, solvent-free clear coat systems are of particular importance.

The coatings, in particular as thin layers, are suited for active, demanding tasks. They protect underlying substrates from the mentioned chemical influences, in particular also from electrochemical and mechanical influences, and/or give objects a particular color and/or a particular surface gloss.

In particular the uppermost coating layers, and in the present case very particularly the clear coat films, are exposed to strong influence from UV radiation, heat, cold, moisture, and oxygen, in addition to acids and bases as well as mechanical stresses, for which reason it is important here to produce particularly strong, irreversibly crosslinked, chemically resistant layers which also have high mechanical resistance.

Due to the emissions problems from solvent-based coating systems and the trend toward simplified and energy-efficient processes, radiation-curing coatings, in particular UV-curing systems, using so-called reactive diluents which dissolve the binder and then polymerize into the network during the crosslinking are becoming increasingly important.

Radiation curing, in particular UV curing via active crosslinking vinyl functional groups, already has widespread industrial application. Mentioned as examples are JP 2008-274209 A, EP 1 333 047 A1, JP 7-069686 A, WO 93/09084 A1, and DE 24 41 600 A1; the number of applications filed worldwide in recent years also generally reflects the practical relevance and the economic significance of radiation-curing systems.

A general treatise on UV-crosslinking systems is provided in "UV-Coatings" by Reinhold Schwalm, Elsevier-Verlag, Amsterdam, 2007.

Although the mechanical properties as well as the achievable surface gloss of radiation-curing clear coats are quite satisfactory, the chemical resistance, in particular the resistance to alkaline and acidic agents, is still regarded as inadequate, in particular with regard to the criteria specified by the automotive industry.

Further current aspects of the UV curing of polymers is described in DE 10 2006 049 764 A1, according to which, for example, aqueous polyurethane dispersions based on unsaturated polyesters are used for UV-crosslinking systems.

Although the use of aqueous dispersions according to DE 10 2006 049 764 A1 addresses the conservation of solvents with regard to pollution control, from the standpoint of energy efficiency it is viewed critically due to the necessary drying step at higher temperatures, or drying times.

DE 10 2004 053 186 A1 describes water- and cosolvent-free UV-curing formulations based on polymerizable urethane acrylates and unsaturated polyesters.

However, polymers based on polyesters are hardly recommendable due to the limited hydrolysis stability with respect to acids and bases.

WO 2008/049932 A1 describes radiation-curing mixtures, containing low-molecular ethylenic fractions, which are suitable as pressure-sensitive adhesives. These low-molecular fractions are incorporated into the network during the crosslinking. As a rule, formulations having very good curing characteristics may thus be obtained, although incompatibilities and difficulties regarding the degree of curing may often occur.

Low-molecular liquid acrylate-/methacrylate-functional compounds are often used in these systems as reactive diluents for the likewise acrylate-functional binders. In particular hexanediol diacrylate (HDDA), for example marketed by BASF SE under the trade name Laromer® HDDA, is very common in this regard.

In WO 2004/000794 A1, compounds having allyl functionalities are obtained by reacting unsaturated alcohols with diisocyanates, the linking of the double bond functionality in the molecule being achieved in each case via a carbamate oxygen atom. Use of these compounds actually results in an improvement in the chemical resistance, but not in the resistance to acids, which is not significantly influenced.

The solubility and compatibility of these compounds in the commercially available UV-crosslinking paint systems is problematic. Since these compounds are synthesized via diisocyanates, the selection of the molecular main body is restricted to the commercially available diisocyanates, which greatly limits a targeted adjustment of the compatibility, or variation in the paint properties.

Another disadvantage is that multiple functional bonds of allyl groups in these compounds are difficult to react in practice, since on the one hand the availability of trifunctional or higher-functional isocyanates is even more limited than for the diisocyanates, and on the other hand these compounds have a strong tendency toward polymerization. However, since the number of vinyl/allyl functionalities per molecule influences the crosslinking density and thus has a crucial effect on the mechanical properties and chemical resistance of the UV-crosslinking paint layers via the functionality of the double bonds, only limited improvements in the chemical resistance are achievable with these compounds as well.

WO 93/09084 A1 is directed to systems for manufacturing contact lenses, and describes compounds containing vinyl carbamate groups for the UV curing of styrene/acrylate/vinyl monomer mixtures for hydrogels. Compounds that are particularly suitable for these monomer mixtures are described which contain at least one vinyl group, it being necessary to select a second group from the functionalities of a styrene group or acrylate group.

For most UV-crosslinking paint systems, however, a styrene functionality is viewed critically, since this often results in incompatibility with existing UV-crosslinking paint systems based on HDDA.

It is an object of the present invention to propose a compound which is suitable as an additive, and whose chemical main body allows modifications of the overall structure of the compound in order to ensure sufficiently high compatibility with as many binder systems as possible. The UV-crosslinkable double bond should be as sterically undemanding as possible, be linked via flexible bonds, and be highly reactive.

This object is achieved by a novel compound having the features of Claim 1.

By using compounds of formula A according to the invention, in particular the compatibility as well as the crosslinking density may be improved compared to the compounds proposed in WO 2004/000794 A1.

According to the invention, the allyl double bond functionality is linked via the carbamate nitrogen atom, not the carbamate oxygen atom. This altered linkage of the double bond functionality may be achieved by reacting allyl-functional isocyanates or amines with corresponding alcohols or the chloroformates thereof.

For the compound according to the invention, an N-functional bond of the allyl functionality to the carbamate group is important, since particularly high chemical stabilities are thus achieved, as will be shown below in conjunction with Example 7.

As a result of this altered linkage of the functional double bond, the compound according to the invention may now be formed from a wide variety of commercially available alcohol-functional starting compounds.

Low-molecular compounds according to the invention, in particular those in which the radical R1 is derived from a $C_2$-$C_5$ hydrocarbon unit, are typically liquid, and are therefore readily usable as reactive diluents in coating compositions.

The at least one ethylenically unsaturated bond (vinyl function) of the radical R1 is preferably selected from N-allyl, N-allyl carbamate, N-vinyl, (meth)acrylate, and/or (meth)acrylamide functions.

Preferred compounds according to the invention are selected in such a way that they are soluble in particular in acrylate-based reactive diluents.

Higher-molecular compounds according to the invention are also used in this manner in liquid coating compositions.

In preferred compounds according to the invention, the radical R1 includes a polyol-based radical.

The polyol-based radical may be selected in particular from diols, triols, oligomeric or polymeric vinyl alcohol compounds, mono-, di-, and polysaccharides, and derivatives of the above-mentioned polyols.

In the case of the selection of mono- and disaccharides, these are preferably used in the form of their sugar alcohols.

The polyol particularly preferably has a molar mass of approximately 3000 g/mol or less, in particular approximately 800 g/mol or less, more preferably approximately 500 g/mol or less.

It has proven to be particularly important that for the compound according to the invention, good copolymerization is ensured even with non-acrylate double bond functions.

The compound according to the invention is very well suited as a component of UV-crosslinking clear coat systems using customary reactive diluent systems, since they are soluble or at least sufficiently compatible so that separation effects may be largely avoided.

In addition, the compound according to the invention has a double bond functionality which allows good copolymerization with the customary acrylate-functional binders and further reactive diluents, these preferably being linked, at least partially, via bonds that are stable with respect to acid/base hydrolysis.

A preferred additional functionalization with acrylate groups is easily possible for the compound of formula A according to the invention, and may significantly increase the compatibility of the compound according to the invention with given paint components. This aspect is important in particular for solvent-free UV-crosslinking clear coats, since in this case extremely high demands are imposed with regard to mechanical stability, homogeneity, clarity, and surface gloss.

The introduction of additional vinyl groups, in particular additional N-vinyl carbamate groups, into the molecule in question is possible, and for certain paint systems may be advantageous for further increasing the crosslinking density.

In the preparation of the compound according to the invention, when amines having a plurality of double bonds are reacted with chloroformates synthesized from diols, compounds having four hydrolysis-stable allyl carbamate functions in the molecule are easily obtainable.

As a result of the greatly expanded selection of molecular overall structures based on the main body of formula A according to the invention, and the variation options with regard to the number and type of further linkable double bond functions, the possibilities for optimizing a UV-crosslinking paint layer with respect to the network density, compatibility, flexibility of the coating, and required chemical resistance are greatly increased, compared to the O-allyl carbamate-functional compounds described in WO 2004/000794 A1, when the N-allyl carbamate-functional compounds according to the invention are used.

Since vinyl-/allyl-functional compounds generally have poor and incomplete curing and crosslinking characteristics in radical curing processes without the presence of certain other double bond functions, but in certain mixtures, for example containing acrylates, the curing proceeds particularly quickly and effectively, in one variant of the compounds according to the invention one or more acrylate functions is/are additionally integrated into the molecule.

These acrylate groups may be linked via an ester bond, since the acid stability of the paint layer is generally ensured by the N-allyl group, already present in the molecule, which is linked via a carbamate group.

The acrylate functions are preferably coordinated with the allyl functionalities in order to optimize the crosslinking.

It has been proven advantageous when the ratio of the N-allyl carbamate functionalities to the acrylate functionalities in the radical R1 is ≥1.

An additional strong compatibility-promoting effect in the customary systems based on acrylate crosslinking also plays a role in the acrylate functionalities (see Example 7).

It is difficult or impossible to take these aspects into account in cited WO 2004/000794 A1, and in particular the mentioned mixed acrylate ester-/O-allyl-functional substances are very difficult to prepare using the reaction process described in WO 2004/000794 A1.

However, in the reaction according to the invention of alcohol components with allyl isocyanates, the mixed acrylate ester/N-allyl compounds are easily obtainable by a reaction involving a maximum of two steps (see Example 2).

In another variant according to the invention, the allyl functionality is linked to a nitrogen atom which is incorporated into a heterocyclic system, in particular a triazine compound. The triazine compounds may be present in tautomeric form. In the present context, the term "triazine" is intended to also always include tautomeric forms, even if, for the sake of simplicity, this is not always explicitly indicated below.

As an N-allyl component, triallyl isocyanate (1,3,5-triallyl-1,3,5-triazine-2,4,6 (1H,3H,5H)trione) or the tautomeric form thereof (see formula 1) is named as an example of this embodiment.

The described N-allyl-functional triazine may be easily prepared from allyl isocyanates under appropriate basic catalysis, and is commercially available.

Formula 1

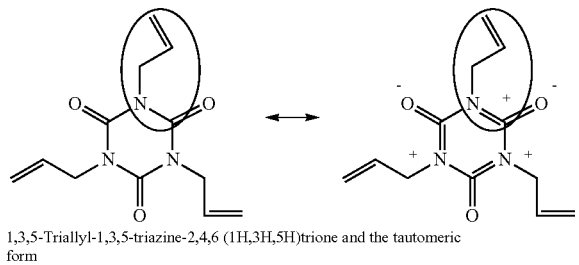

1,3,5-Triallyl-1,3,5-triazine-2,4,6 (1H,3H,5H)trione and the tautomeric form

The novel compounds of the bifunctional, trifunctional, and higher-functional N-allyl carbamates may generally be easily prepared by reacting allyl isocyanate and an aliphatic linear, mono- or bicyclic or heterocyclic polyol.

As polyols, monomeric polyhydric alcohols (diols and triols, for example), saccharides and derivatives thereof, in particular sugar alcohols, as well as copolymers prepared using vinyl acetate may be used, for the latter the alcohol functionalities being formed by acid- or base-catalyzed hydrolysis/solvolysis reactions.

When the alcohol groups are used in stoichiometric excess relative to the allyl isocyanate, for example, the remaining OH groups may be reacted in a second reaction step using acrylic chloride or methacrylic chloride, for example, under amine catalysis. The mixed N-allyl or acrylate ester compounds described above, likewise according to the invention, are thus obtained.

As previously described, the compounds according to the invention may also be obtained via the corresponding polyol-containing chloroformate by reaction with allyl amines.

The latter method is suited primarily for preparing particularly high-functional allyl carbamates according to the invention, or short-chain novel N-allyl carbamate-functional compounds for radical- and radiation-curing systems (Example 3).

In principle, the mentioned N-allyl-functional compounds or mixtures thereof may be used in all radiation-curing systems as well as electron beam-curing systems, wherein acrylate-functional systems, in particular UV-curing coatings, are preferred.

It is particularly preferred to use these compounds in solvent-free UV-curing clear coat formulations (see Example 6), since in this case other additives, for example buffering or matrix-reinforcing pigments and fillers, cannot be used due to the stringent requirements for transparency.

The N-allyl-functional compounds are also used in UV-crosslinking inks, powder coatings, or in general in UV-crosslinking polymer matrices of all types.

Based on the above discussion, it is apparent that another important aspect of the invention lies in providing a composition which includes one or more of the compounds, described in detail above and defined in Claims 1 to 10, which may be advantageously used in radiation-curing coatings.

Alternatively or preferably additionally, such compositions contain a compound that is selected from monomeric, oligomeric, and polymeric N-vinyl- or N-allyl-functional 1,3,5-triazine compounds, in particular 1,3,5-triallyl-1,3,5-triazine-2,4,6-(1H,3H,5H)trione.

The compositions according to the invention are preferably solvent-free.

The use of triallyl isocyanate is typically described in conjunction with organic sulfur compounds in UV-curing systems (see, for example, JP 57-133108 A, JP 57-158230 A, JP 58-213022 A, FR 2258436 A1, DE 24 02 390 A1, U.S. Pat. No. 3,855,093 A), wherein the curing process proceeds not by UV radical curing as in the present invention, but, rather, by UV cationic curing.

However, use of the usually toxic and environmentally harmful organic sulfur compounds must be viewed critically in the future, since in particular the coatings industry has an interest in the concepts of zero emissions as well as wastewater control. However, the use of UV-curing clear coat layers containing organic sulfur compounds conflicts with such a concept, and is less suitable for an environmentally friendly coatings technology, particularly since the sulfur compounds may sometimes leach from the coating.

Thus, for radiation-curing paint layers, in particular for the UV-curing clear coats of interest from an environmental and economic standpoint, the processes for UV curing of polymers described in the above-cited publications do not represent a meaningful alternative approach.

In EP 1 111 008 A1, EP 1 338 623 A1, and EP 1 674 513 A1, triallyl isocyanate has also been described as a component of UV radical-curing mixtures for producing thermoplastics and/or elastomers.

These methods basically concern thick-layered, uncrosslinked or weakly crosslinked polymer applications, and are not suitable for producing thin-layered, strongly crosslinked coatings which are stabilized with respect to UV and weathering effects as well as mechanically resistant.

Compounds having a fairly high molecular weight are less suited for meeting the requirements for the resulting coatings and clear coat layers, since in the established radiation-curing formulations the solubility and compatibility generally decrease with increasing molar mass, while the viscosity greatly increases.

A great increase in viscosity in the UV paint preparations is usually associated with poor flow, low surface gloss values, and lower mechanical and chemical stability, which is particularly problematic for clear coat coatings.

For this reason, low-molecular and in particular monomolecular compounds are preferably used which have a molecular weight less than 5000 g/mol, more preferably less than 1000 g/mol, and in particular less than 700 g/mol.

Mixtures of the described N-allyl-functional substances may also be advantageous in specialized compositions in order to greatly improve the polymerization of the individual components by copolymerization.

Based on the previous explanation of the compounds and compositions according to the invention, it is apparent that another important aspect of the present invention lies in providing coating compositions as defined in Claim 14.

Accordingly, substantially solvent-free compositions are preferred. These compositions may in particular also include one or more further reactive diluents.

Other reactive diluents suitable within the scope of the invention include, among others, the previously mentioned hexanediol diacrylate (HDDA), hexamethylene diol dimethacrylate (HDDMA), isobornyl acrylate (IBOA), tripropylene glycol diacrylate (TPGDA), and trimethylolpropane triacrylate (TMPTA).

In the mixture of the compound according to the invention with a further reactive diluent, the proportion of the compound according to the invention and/or of the N-vinyl-, N-allyl-functional 1,3,5-triazine compounds is preferably approximately 5% to approximately 80% by weight, and in some applications is even higher.

Suitable reactive diluents also include 2,4,6-triallyloxy-1,3,5-triazine (formula 2) as a commercially available example of an O-allyl-functional compound that is likewise based on a triazine main body, although with respect to the N-allyl-functional compounds according to the invention, this reactive diluent used alone provides less satisfactory results with regard to caustic resistance, acid resistance, and/or scratch resistance (see Example 7).

The reactive diluent of formula 2 is suitable in particular for UV-curing coating compositions which are used at higher temperatures, for example 60 to 80° C.

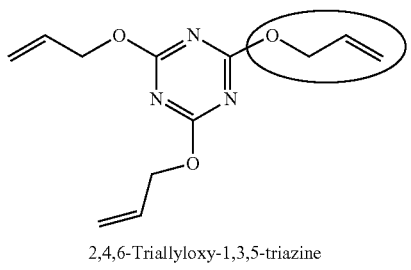

2,4,6-Triallyloxy-1,3,5-triazine

Formula 2

In addition, the coating compositions according to the invention preferably include a polymer- or oligomer-based binder.

Such binders preferably include an acrylate-, urethane-, or polyester-functional binder.

The coating compositions according to the invention are particularly suited for producing coatings having layer thicknesses of approximately 0.5 μm to approximately 600 μm, more preferably approximately 0.5 μm to approximately 100 μm.

The coating compositions according to the invention are also preferably formulated as a paint, in particular as a clear coat. Clear coat formulations that are UV-curable, more preferably UV radical-curable, are particularly preferred.

The coating compositions according to the invention are likewise preferably formulated as ink.

Preferred UV radical-curable coating compositions according to the present invention include an N-allyl carbamate-functional compound according to one of Claims 1 to 10 as an aliphatic reactive diluent component, the radical R1 being derived from a $C_2$-$C_5$ hydrocarbon unit, and/or the coating compositions include a triallyl triazine compound (optionally in tautomeric form).

The N-allyl carbonate-functional compounds according to the invention having a radical R1 that is derived from a $C_2$-$C_5$ hydrocarbon unit are typically liquid, and thus are also suitable as the sole reactive diluent in the coating compositions according to the invention.

The above-mentioned coating compositions according to the invention are preferably characterized in that the proportion of the compound according to one of Claims 1 to 10 is approximately 80% by weight or less, in particular approximately 5 to 60% by weight, more preferably approximately 8 to 30% by weight, or the proportion of the composition according to one of Claims 11 to 14 is approximately 80% by weight or less, in particular approximately 5 to 60% by weight, more preferably approximately 25 to 60% by weight, most preferably approximately 30 to 60% by weight.

The following examples are intended to explain the invention in greater detail without limiting the invention thereto:

EXAMPLES

Example 1

Synthesis of hexamethylene-bis-N-allyl carbamate 11.4 g hexamethylene diol and 0.01216 g dibutyltin dodecanate (catalyst) were dissolved in 70 g methylene chloride, and 16.0 g allyl isocyanate was added dropwise with ice cooling.

After stirring for 20 hours at room temperature under a nitrogen atmosphere, the methylene chloride was stripped under vacuum. The obtained product was washed with warm distilled water at a temperature of 50° C. until the wash water was pH-neutral.

Drying was then performed, using $Na_2SO_4$. The product was identified by proton resonance spectroscopy.

Example 2

Synthesis of acryloyl hexamethylene-N-allyl carbamate 12.8 g hexamethylene diol was dissolved in 150 g methylene chloride, and 9.0 g allyl isocyanate was added dropwise with ice cooling.

After heating for 20 hours at 35° C. under a nitrogen atmosphere, the mixture was once again cooled with ice water, 15 mL diisopropylethylamine was added, and 9.8 g acryloyl chloride was added dropwise.

The mixture was stirred for 20 hours at room temperature, and the methylene chloride was stripped under vacuum.

The resulting product was washed by shaking with cold water until the wash water showed a neutral pH.

The mixture was then diluted with approximately the same quantity of butyl acetate, and was shaken out three times with cold water.

After drying over magnesium chloride, the butyl acetate was carefully stripped under vacuum at the lowest possible temperature. The product was identified by proton resonance spectroscopy.

Example 3

Synthesis of 1,4-tetramethylene-bis-(diallylamino)carbamate

A solution of 10.0 g diallylamine, followed by 12 mL diisopropylethylamine in 80 mL methylene chloride, were added dropwise to a solution of 10.0 g butanediol-bis-chloroformate in 54 mL methylene chloride cooled with ice water.

After stirring for 20 hours at room temperature, the methylene chloride was stripped under vacuum, and the product was carefully washed with warm distilled water at a temperature of 50° C. until the wash water was pH-neutral.

Drying was then performed, using $Na_2SO_4$. The product was identified by proton resonance spectroscopy.

Reference Example 4

Synthesis of 1,6-hexamethylene-bis-allyl carbamate

According to WO 2004/000794 A 1

20.0 g hexamethylene diisocyanate was added dropwise to 14.0 g allyl alcohol and 0.0152 g dibutyltin dodecanate in 70 g methylene chloride, with ice cooling.

After stirring for 20 hours at room temperature under a nitrogen atmosphere, and stripping the methylene chloride under vacuum, the product was washed by shaking several times with warm distilled water at a temperature of 50° C. until the wash water was pH-neutral.

Drying was then performed, using $Na_2SO_4$. The product was identified by proton resonance spectroscopy.

Reference Example 5

Synthesis of N,N-isophorone-bis-allyl carbamate

According to WO 2004/000794 A 1

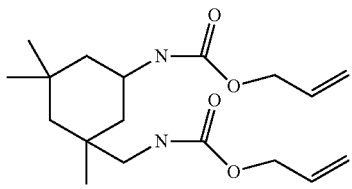

Formula 3

N,N-isophorone-bis-allyl carbamate (WO 2004/000794 A1)

26.7 g isophorone diisocyanate was added dropwise to 14.0 g allyl alcohol and 0.0152 g dibutyltin dodecanate, with ice cooling.

After stifling for 20 hours at room temperature under a nitrogen atmosphere, the product was washed by shaking several times with warm distilled water at a temperature of 50° C. until the wash water was pH-neutral.

Drying was then performed, using $Na_2SO_4$. The product was identified by proton resonance spectroscopy.

Example 6

Processing of the Compounds from Examples 1 to 5 and Additional Commercially Available Components to Form Coating Formulations Desmolux® U 880H from Bayer MaterialScience was used as binder, Laromer® HDDA from BASF was used as reactive diluent, and BYK 306 from BYK Altana was used as flow control additive for the radiation-curing test formulations in this example.

To produce the coating formulations, the above-mentioned coating components, the UV crosslinker Irgacure 184 from Ciba, and optionally a compound obtained in Examples 1 to 5, i.e., 1,3,5-triallyl-1,3,5-triazine-2,4,6 (1H,3H,5R)trione (Aldrich) as N-allyl-functional triazine compound or 2,4,6-triallyloxy-1,3,5-triazine (Aldrich) as O-allyl-functional triazine compound, were mixed according to the proportions listed in Table 1 in a high-speed stirrer having a toothed disk for 15 min at a disk peripheral speed of 1.0 m/sec.

The standard formulation listed in Table 1 represents the base formulation, which in each case was varied by replacing 50% of the HDDA component in order to test the compounds of Examples 1 to 5 and the other two triazine compounds with regard to their functioning in the coating system; these are also referred to in the table as replacement additives.

The obtained test formulations were applied, using a doctor blade having a 50-μm gap, to panels prepainted black (for example, the black portion of panels available under the trade name Leneta panel Form M12, black and white spray monitor).

The radiation curing was performed by UV radiation (undoped high-pressure mercury lamp) of the applied paint layers at room temperature, with a UV dose of 1800 mJ/cm² in an inert $N_2$ atmosphere.

TABLE 1

| Paint component | Standard formulation | Modified formulation |
|---|---|---|
| Desmolux U 880H [% by weight] | 59.70 | 59.70 |
| Byk 306 [% by weight] | 0.93 | 0.93 |
| Irgacure 184 [% by weight] | 2.89 | 2.89 |
| Laromer HDDA [% by weight] | 36.48 | 18.24 |
| Replacement additive [% by weight] | — | 18.24 |

Example 7

Results of Testing of the Paint Layers

The testing of the alkali/acid resistance of the paint samples produced in Example 6 was conducted by dripping a one-percent sodium hydroxide solution or sulfuric acid solution onto the samples.

The coatings treated in this manner were exposed to a temperature gradient for 30 min in a gradient oven. The stressed surfaces were rinsed with water and dried, and after 24 hours storage at 23° C. and 50% relative humidity, the damage was visually evaluated.

For the alkali and acid resistance of the coating, the lowest temperature was determined at which damage was visually detectable.

When the obtained acid and alkali stabilities of the standard formulation were compared to the stabilities for the coatings which resulted from replacing 50% of the HDDA fraction with the replacement additives, an alkaline temperature stability of 41° C. and an acid stability of 42° C. were obtained for the standard formulation containing HDDA.

For the paint layer modified with the N-allyl-functional triazine compound, a high alkaline temperature stability of 61° C. and an increased acid stability of 47° C. were detected.

For the O-allyl-functional triazine compound, for 50% replacement of HDDA a lowered alkaline temperature stability of 59° C. and a likewise lowered acid resistance of 44° C. compared to the N-allyl-functional triazine were obtained as the result.

However, the N-allyl-functional triazine compound shows advantages over the O-allyl-functional triazine compound not just with respect to the chemical resistance. When a 300-hour short-term weathering test of the obtained paint layers was conducted according to DIN EN ISO 11341, when the O-allyl-functional triazine was used, a color change ΔE increase by 0.35 units was observed after the weathering (measuring geometry d/8°, color I5, GretagMacbeth).

This indicates higher weathering stability of N-allyl-functional triazines compared to O-allyl-functional triazine compounds.

When other O-allyl-functional substances which according to cited WO 2004/000794 A1 may be prepared from diisocyanates and allyl alcohols were tested for suitability in a UV-curing clear coat application, when the cyclic N,N-isophorone-bis-allyl carbamate from Example 5 (formula 3) was used, an alkaline temperature stability of only 54° C. and an acid stability of once again only 44° C. were obtained when 50% of the HDDA was replaced.

Analogously to the N,N-isophorone-bis-allyl carbamate, the hexamethylene-bis-allyl carbamate (Example 4) was obtained by reacting the corresponding hexamethylene diisocyanate with allyl alcohol according to WO 2004/000794 A1. This sample was incompatible with the paint system, and was not directly soluble in HDDA, and the corresponding N-allyl-functional hexamethylene-bis-N-allyl carbamate from Example 1 likewise was not directly soluble in HDDA, so that as a whole, an incompatibility-promoting effect of the hexamethylene main body may be concluded.

To still be able to test the influence on the chemical resistance, the hexamethylene-bis-allyl carbamate from Example 4 was dissolved in methanol beforehand and applied, and prior to the UV-crosslinking, the paint layer was dried under vacuum at 50° C. for several hours to remove the methanol.

Although transparent paint layers were obtained, surprisingly an alkali resistance of 45° C. and an acid resistance of 44° C. were obtained which were only slightly improved compared to the standard paint.

When only a portion of the allyl carbamate functions according to the invention were replaced with acrylate groups, the compounds were more compatible with the paint system, and, compared to the hexamethylene-bis-allyl carbamate from Example 4 according to WO 2004/000794 A1, surprisingly the alkali resistance of the paint layer increased from 45° C. to 48° C. when the substance obtained from Example 2 was incorporated, while the acid resistance remained constant at 44° C.

Based on this result, it may be concluded that the compatibility of a compound apparently strongly influences the achievable chemical resistance of the paint layer, and that the influence of the compatibility of a compound may have a greater effect than a hydrolysis-stable linkage of the double bond functionality.

In addition, combining monomer units which copolymerize well in the same molecule appears to have positive effects on the achievable chemical resistance.

To explain the influence of the hexamethylene main body and the double bond functionality in greater detail, in Example 3 a corresponding tetra-functional N-allyl carbamate, 1,4-tetramethylene-bis-(diallylamino)carbamate, was synthesized via a tetramethylene diol chloroformate. The obtained compound was liquid at room temperature and completely miscible with the reactive diluent HDDA. For the resulting paint system, a relatively high value of 56° C. was obtained for the alkali resistance, while a value of 44° C. was obtained once again for the acid resistance.

It is also possible to directly use the tetrafunctional N-allyl carbamate, without HDDA, obtained from Example 3, as the sole reactive diluent, since it is present as a liquid and shows good dissolving capability for UV initiators and a high degree of compatibility with customary binder systems. This also allows use in high concentrations, for example 80% by weight, in the coating composition.

Combining the obtained results allows a conclusion that the hydrolysis-stable linkage of the double bond functions to be crosslinked, their functionality in the molecule, and the main body used play an important role.

The results indicate that the use of ring structures, in particular heterocycles and, more preferably, triazine compounds, as the main body, functionalized with higher-functional, hydrolysis-stable allyl groups linked via carbamate groups has a particularly advantageous effect for a very high acid and base stability.

However, to achieve excellent chemical stability, according to the invention the mentioned compatibility and reactivity of a corresponding compound, for example by additional modification with acrylate functionalities, may also be adapted to the present paint system in a targeted manner.

In this regard, it is important to ensure the correct ratio of hydrolysis-stable allyl carbamate functionalities to the acrylate functionalities in the paint system so that optimal copolymerization of the components may be achieved.

If the additives are to be used in existing paint formulations, other paint properties should not be adversely affected by the addition of additive.

Surprisingly, for the paint layer produced using the N-allyl-functional triazine, an improved scratch resistance of almost 53 mN up to the initial crack formation (crack formation of standard coating at 51 mN) was also measured using a model UNHT instrument from CSM Instruments.

For the paint layer modified with the O-allyl-functional triazine, a greatly reduced scratch resistance was observed with an initial crack formation at 31 mN.

The above-described test results are summarized in Table 2.

TABLE 2

| Paint composition with replacement additive | Caustic resistance [° C.] | Acid resistance [° C.] | Scratch resistance [mN] |
|---|---|---|---|
| Without (standard) | 41 | 42 | 51 |
| From Example 1 | Incompatible with paint system | | |
| From Example 2 | 48 | 44 | —**) |
| From Example 3 | 56 | 44 | —**) |
| From Example 4*) (reference) | 45 | 44 | —**) |
| From Example 5 (reference) | 54 | 44 | 50 |
| Of formula 1 N-allyl-functional triazine | 61 | 47 | ~53 |
| Of formula 2 (reference) O-allyl-functional triazine | 59 | 44 | 31 |

*)Modified processing; see description
**)No values were determined

In the testing of the important paint properties, such as surface gloss and loss of gloss (HazeGloss, Byk Gardner) or hardness and loss of hardness after weathering (Fischerscope H100, Fischer), no negative effects on the paint layer could be detected for the additives according to the invention, up to a 50% replacement of HDDA in the tested formulation.

Thus, the novel additives primarily improve the chemical resistance and the mechanical resistance, but without significantly influencing the weathering stability or the surface gloss. Therefore, they may be used particularly advantageously as additives in paint systems, in particular in UV clear coat systems.

The invention claimed is:

1. A composition for use in radiation-curing coatings comprising a 1,3,5-triazine compound selected from 1,3,5-triallyl-1,3,5-triazine-2,4,6(1H,3H,5H)trione and the tautomeric form thereof and a reactive diluent selected from hexamethylene diol diacrylate (HDDA), hexamethylene diol dimethacrylate (HDDMA), isobornyl acrylate (IBOA), tripropylene glycol diacrylate (TPGDA), and trimethylolpropane triacrylate (TMPTA).

2. The composition according to claim 1, wherein the composition is composed substantially of compounds having a molar mass of approximately 1000 g/mol or less.

3. The composition according to claim 1, wherein the composition is substantially solvent-free.

4. The composition according to claim 1, wherein the composition includes a polymer- or oligomer-based binder.

5. The composition according to claim 4, wherein the binder includes an acrylate-, urethane-, or polyester-functional binder component.

6. The composition according to claim 1, wherein the proportion of the compound in the composition is approximately 80% by weight or less.

7. The composition according to claim 6, wherein the proportion of the compound in the composition is approximately 5 to 60% by weight.

8. The composition according to claim 7, wherein the proportion of the compound in the composition is approximately 8 to 30% by weight.

9. The composition according to claim 1, wherein the composition is free from organic sulfur compounds.

10. The composition according to claim 1, wherein the composition formulated as paint.

11. The composition of claim 10, wherein the paint is a clear coat.

12. UV radical-curable coating composition comprising a 1,3,5-triazine compound selected from 1,3,5-triallyl-1,3,5-triazine-2,4,6 (1H,3H,5H)trione and the tautomeric form thereof and a reactive diluent selected from hexamethylene diol diacrylate (HDDA), hexamethylene diol dimethacrylate (HDDMA), isobornyl acrylate (IBOA), tripropylene glycol diacrylate (TPGDA), and trimethylolpropane triacrylate (TMPTA).

13. The composition according to claim 12, wherein the composition is composed substantially of compounds having a molar mass of approximately 5000 g/mol or less.

14. The composition according to claim 13, wherein the composition is composed substantially of compounds having a molar mass of approximately 1000 g/mol or less.

15. The composition according to claim 12, wherein the coating composition is substantially solvent-free.

16. The composition according to claim 12, wherein the coating composition includes a polymer- or oligomer-based binder.

17. The composition according to claim 16, wherein the binder includes an acrylate-, urethane-, or polyester-functional binder component.

18. The composition according to claim 12, wherein the proportion of the compound in the coating composition is approximately 80% by weight or less.

19. The composition according to claim 18, wherein the proportion of the compound in the coating composition is approximately 5 to 60% by weight.

20. The composition according to claim 19, wherein the proportion of the compound in the coating composition is approximately 8 to 30% by weight.

21. The composition according to claim 12, wherein the coating composition is free from organic sulfur compounds.

22. The composition according to claim 12, wherein the coating composition is formulated as paint.

23. The composition of claim 22, wherein the paint is a clear coat.

* * * * *